United States Patent
Fields

(10) Patent No.: US 6,586,250 B1
(45) Date of Patent: Jul. 1, 2003

(54) METHOD OF PCR-BASED GENE TARGETING

(75) Inventor: Larry E. Fields, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 08/440,566

(22) Filed: May 16, 1995

(51) Int. Cl.[7] .................. C12N 15/85; C12N 15/90; C12N 5/18
(52) U.S. Cl. .................. 435/463; 435/91.2; 435/354
(58) Field of Search ................ 435/91.2, 172.3, 435/240.2

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis et al. | 435/91.2 |
| 5,850,004 A | * 12/1998 | MacMicking et al. | |

OTHER PUBLICATIONS

Miller et al. (1992), Proc. Natl. Acad. Sci. USA 89:5020–5024.*
Mansour et al. (1988), Nature 336:348–352.*
Tybulewicz et al. (1991), Cell 65: 1153–1163.*
Arnheim et al., Chem. & Engr. News, Oct. 1, 1990, pp. 36–47.
Cheng et al., (1994) Proc. Natl. Aca. Sci. USA 91, 5695–5699.
Feldman, Chem. & Engr. News, Dec. 20, 1993, pp. 26–38.
Bronson et al., (1994) J. Biol. Chem. 269, 27155–27158.
Melton, D. W. (1994) Boessays 16, 633–638.
Shastry, B.S. (1994) Mol. Cell. Biochem. 136, 171–182.
Robbins, J. (1993) Circ. Res. 73, 3–9.
Thomas et al., (1987) Cell 51, 503–512.
Kuida et al., (1995) Science 267, 2000–2003.
Chartrain et al., (1994) J. Biol. Chem. 269, 6765–6772.
Geller et al., (1993) Proc. Natl. Acad. Sci. USA 90, 3491–3495.
Xie et al., (1992) Science 256, 225–228.
Raschke et al., (1978) Cell 15, 261–267.
Reaume et al., (1995) Science 267, 1831–1834.

* cited by examiner

*Primary Examiner*—Remy Yucel
*Assistant Examiner*—Bronwen M. Loeb
(74) *Attorney, Agent, or Firm*—Scott J. Meyer

(57) ABSTRACT

An improved method of gene targeting, referred to as PCR-based gene targeting is disclosed, which generates cell lines or mice in which at least one allele of a specific gene is disrupted by double homologous recombination of a PCR-derived targeting vector with chromosomal DNA. The method is especially applied to murine macrophage cytokine-inducible nitric oxide synthase (MøiNOS).

4 Claims, 5 Drawing Sheets

METHOD OF PCR-BASED GENE TARGETING

BACKGROUND OF THE INVENTION

This invention relates to an improved method of gene targeting that is more rapid and less costly than conventional gene targeting. More particularly, the invention relates to a PCR-based gene targeting method to develop cell lines and mice in which at least one allele of a specific gene is disrupted by double homologous recombination of a PCR-derived targeting vector with chromosomal DNA. The method of the invention is especially applied to murine macrophage cytokine-inducible nitric oxide synthase (Mø-iNOS).

PCR (polymerase chain reaction) is an in vitro method of amplifying DNA sequences. It is an enzymatic process that is carried out in discreet cycles of amplification, each of which can double the amount of target sample. For a brief recent review, see Arnheim and Levenson, "Polymerase Chain Reaction", *Chem. & Eng. News*, Oct. 1, 1990, pp. 36–47. See also U.S. Pat. Nos. 4,683,195 and 4,683,202.

Long-range PCR is an in vitro method of amplifying longer DNA sequences using a combination of thermostable DNA polymerases. See Cheng et al., *Proc. Natl. Acad. Sci. USA* 91, 5695–5699 (1994).

Nitric Oxide (NO) has been shown to modulate vascular tone, smooth muscle cell proliferation, platelet aggregation and adhesion, leukocyte adhesion, and macrophage (Mø) cell-mediated cytotoxicity. Thus, NO appears to be medically important in vascular biology and immunology. For a recent brief review, see Feldman, Griffith and Stuehr, "The Surprising Life of Nitric Oxide", *Chem. & Eng. News*, Dec. 20, 1993, pp. 26–38.

NO is produced from L-arginine by two classes of NO synthase (NOS). A constitutive NOS (cNOS) is rapidly activated for a very brief duration by an elevation in intracellular $Ca^{2+}$ and calmodulin binding. The activity of cytokine-inducible NOS (iNOS) is slowly increased, due to transcriptional induction, and sustained for days.

The gene for Mø-iNOS has been cloned and shown to be a distinct member of the NOS gene family. Consequently, the iNOS isoform is an attractive potential target for pharmacological modification of inflammation.

(Note: Literature references on the following background information and on conventional test methods and laboratory procedures well known to the ordinary person skilled in the art, and other such state-of-the-art techniques as used herein, are indicated in parentheses, and appended at the end of the specification.)

Gene targeting has been used heretofore to develop animal models of disease, explore mechanisms of biological development, and assess the functional importance of molecules. The subject of gene targeting has been reviewed recently (1–8). This technique makes use of double homologous recombination in murine embryonic stem (ES) cells between chromosomal DNA and homologous sequences in the targeting vector (9–11). Transfected ES cells are screened and those with a correctly targeted allele are injected into blasto-cysts to generate mice having a defined germline mutation.

Conventional targeting constructs consist of neo (neomycin phosphotransferase) positive-selectable marker gene flanked by a total of at least 4 kb (kilobases) of homologous DNA sequence (11).

The tk negative-selectable marker gene is commonly used in conventional targeting constructs (12–19).

The frequency of homologous recombination varies as a function of insertional- versus replacement-vector design (11), length of DNA homology (11, 20, 21), and degree of polymorphic variation between the vector and the chromosome (22).

In conventional targeting, the targeting vector is derived from genomic DNA fragments obtained using conventional library cloning techniques. Typically, the DNA fragments are cloned from isogenic or non-isogenic murine genomic libraries. This process is time consuming and costly, such that commercial businesses have been formed that specifically offer this service at market prices.

Accordingly, a method of gene targeting that is faster and less costly whereby it bypasses the conventional library cloning process would have significant advantages in the field.

BRIEF DESCRIPTION OF THE INVENTION

In accordance with the present invention, a novel method, referred to as PCR-based gene targeting, is provided. According to this method, large DNA fragments homologous to the gene to be targeted, for example the inducible nitric oxide synthase (NOS2) gene locus, are obtained by using long-range PCR (23).

A large PCR-derived amplicon, for example the 7 kb NOS2 homologous amplicon, is used to construct a targeting vector where the neo gene is flanked by PCR-derived homologous DNA sequences. The vector also includes a thymidine kinase (tk) negative-selectable marker gene.

The resulting targeting vector is then transfected into murine ES cells, where homologous recombination takes place. That is, following transfection into ES cells, the PCR-based targeting vector undergoes efficient homologous recombination into the NOS2 locus.

According to a preferred method of the invention, the PCR-based gene targeting comprises the steps of:

(a) obtaining a PCR-derived homologous genomic DNA fragment by applying long-range PCR to a murine genomic DNA template to generate a large genomic amplicon spanning the exons of a gene locus of interest by employing
  (i) a first oligonucleotide primer having a sequence specific for the 5' end of the target region and a suitable restriction site added at its 5' end, and
  (ii) a second oligonucleotide primer having a sequence specific for the 3' end of the target region and a suitable restriction site added at its 3' end, whereby said primers bind to, respectively, the 5' and 3' ends of said target area, (b) producing a PCR-based targeting vector by
  (i) inserting the 1.7 kb pgk-neo positive selectable marker gene into said amplicon at a suitable restriction site within said target region and
  (ii) inserting the 2.6 kb pgk-tk negative selectable marker gene at the 5' or 3' end of said amplicon to linearize said targeting vector, and (c) thereafter transfecting said PCR-based targeting vector into ES cells whereby said targeting vector undergoes efficient homologous recombination into said gene locus.

By the term "large" genomic amplicon is meant an amplicon of at least 4 kb in length. The large genomic amplicon is exemplified by a 7 kb genomic amplicon spanning exons 4 to 7 of the NOS2 gene locus consisting of a 1.1 kb short-arm spanning exons 6 to 7 and a 5.9 kb long-arm spanning exons 4 to 6 of said NOS2 gene locus.

A preferred restriction site added at the 5' end of said first oligonucleotide primer is ClaI; a preferred restriction site added at the 3' end of said second oligonucleotide primer is NotI.

A preferred restriction site within the target region for insertion of the pgk-neo positive selectable marker gene is the SacI site at the 3' end of exon 6 of the NOS2 amplicon.

A preferred murine genomic DNA template is the genomic DNA from the conventional, well-known RAW 264.7 murine macrophage cell line (H-$2^d$) which is readily available from the American Type Culture Collection, Rockville, Md., under Accession Number ATCC TIB 71.

Preferred oligonucleotide primers are shown in the Examples and Table 1, below.

By this method, PCR-based gene targeting is applied to the mouse-inducible nitric oxide synthase locus, whereby ES cell lines are generated in which the NOS2 gene is disrupted on one chromosome.

This method expedites the acquisition of homologous genomic DNA sequences, and simplifies the construction of targeting plasmids by making use of defined cloning sites.

It also provides a substantial time and cost savings for appropriate homologous recombination projects. The PCR-based gene targeting method of the invention thus is a valuable alternative to the conventional cloning approach.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the appended drawings.

Approximate genomic distance between exons was estimated for primer pairs that generated an amplicon (lanes 1, 5, 6, 7, 8, and 9). See Table 1 and Methods below for primer sequences, putative exon locations, and size of amplicons.

The largest amplicon is about 7 kb and includes putative exons 4 to 7 (lane 8). This amplicon was used to construct a gene targeting vector. Size markers are shown in lane M.

Figure 2A:
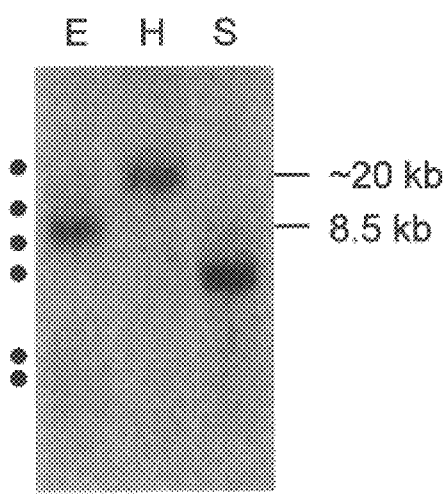
Figure 2B:
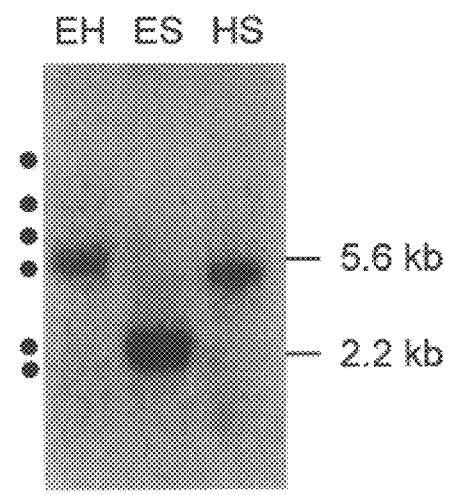

FIG. 2, in two parts, namely, FIG. 2A (panel A) and FIG. 2B (panel B) shows: Validation of PCR-based mapping using in-gel Southern blot analysis where genomic DNA fragment sizes are the same as those estimated by PCR analysis.

(panel A) Murine genomic DNA (8 µg/lane) was digested with EcoRI (E), HindIII (H), or SacI(S).

Figure 3:
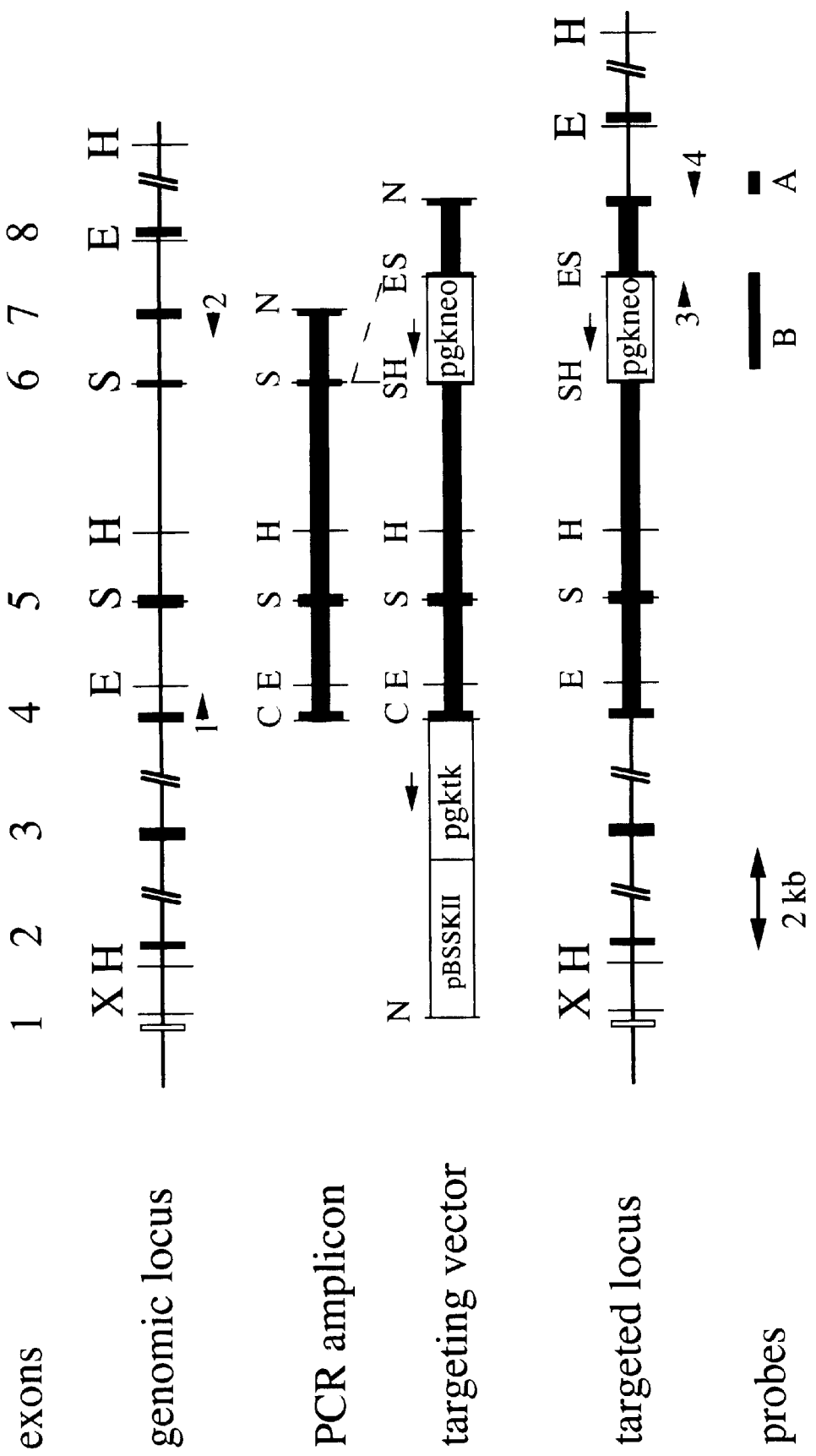

(panel B) DNA was double-digested with EcoRI and HindIII (EH), or EcoRI and SacI (ES), or HindII and SacI (HS). Samples were electrophoresed within the same gel and hybridized with probe A (FIG. 3). Dots represent size markers as described in FIG. 1.

FIG. 3 shows: Schematic diagram of PCR-based gene targeting of the murine NOS2 locus. (exons,genomic locus) Genomic positions of putative exons were determined by the PCR strategy shown in FIG. 1. Distance between exons 2 to 4 is represented by interrupted lines.

The distance between the second and third HindIII (H) sites was determined by Southern blot analysis to be approximately 20 kb. Other restriction sites are ClaI (C), EcoRI (E), NotI (N), SacI (S), and XbaI (X).

For the sake of clarity, only relevant restriction sites are shown. (PCR amplicon)

Primers 1 and 2 (Table 1, Gel Lane 8, primer pairs) are represented by arrow heads and were used to generate a 7 kb amplicon, represented by the shaded bar.

Targeting Vector:

This was constructed by cloning the 7 kb amplicon into a Bluescript vector containing the pgk-tk selection cassette and inserting the pkg-neo selection cassette into the SacI site of exon 6. The targeting vector was linearized with NotI and transfected into ES cells.

Targeted Locus:

The murine NOS2 locus after homologous recombination. Primers 3 and 4 (arrow heads) were used to screen for homologous recombination involving the short-arm.

Probes:

Homologous recombination was confirmed by Southern blot analysis using the 0.3 kb genomic probe A and the 1.7 kb pgk-neo probe B.

Figure 4A:
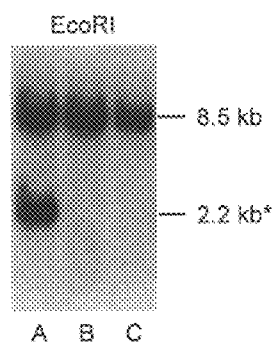
Figure 4B:
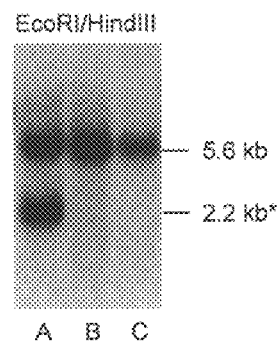
Figure 4C:
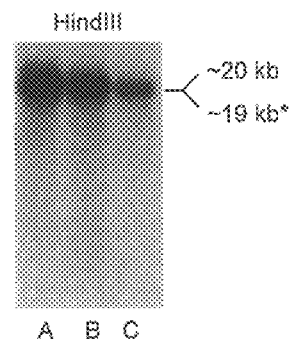

FIG. 4, In three parts, namely FIG. 4A (panel A), FIG. 4B (panel B, and FIG. 4C (panel C) shows: Homologous recombination was detected using Southern blot analysis of genomic DNA from transfected ES cell clones, hybridized with probe A. Genomic DNA was isolated from ES cell clones ROH.1 (lane A), ROH.2 (lane B), and E14.1 (lane C).

Ten micrograms of DNA was digested with EcoRI (panel A), EcoRI and HindIII (panel B), or HindIII (panel C). The band representing the allele that has undergone homologous recombination is marked with an asterisk. Hybridizations were performed simultaneously, using the same probe preparation.

Figure 5A:
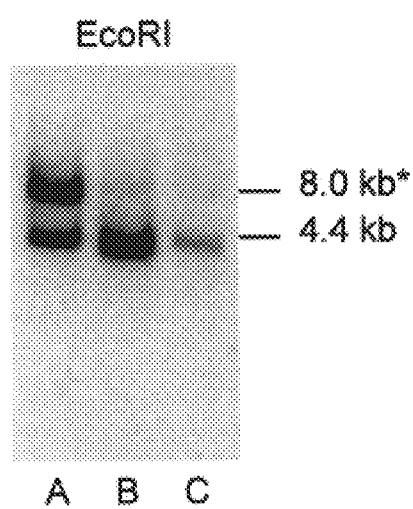
Figure 5B:
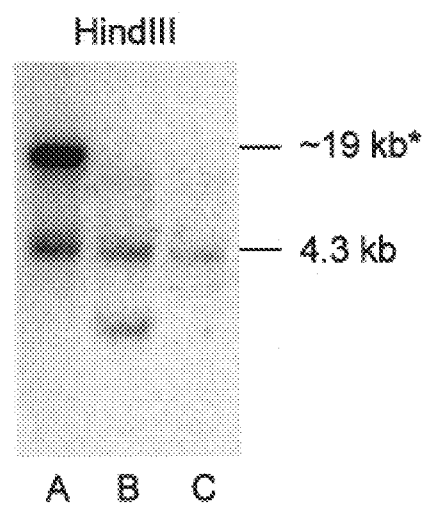

FIG. 5, in two parts, namely FIG. 5A (panel A) and FIG. 5B (panel B) shows: Confirmation of homologous recombination using probe B. Genomic DNA was isolated from ES cell clones ROH.2 (lane A), ROH.1 (lane B), and E14.1 (lane C). Ten micrograms of DNA was digested with EcoRI (panel A) and HindIII (panel B). The band representing the allele that has undergone homologous recombination is marked with an asterisk. Hybridizations were performed as in FIG. 4.

IN ORDER TO ILLUSTRATE the invention in further detail, the following specific laboratory examples were carried out with the results indicated. Although specific examples are thus illustrated, it will be understood that the invention is not limited to these specific examples or the details therein.

EXAMPLES

Materials and Methods

PCR. The genomic organization of the human NOS2 locus (24) and sequences of human (25) and murine NOS2 cDNA's (26–28) were used as a basis for approximating where putative exon boundaries might be. Oligonucleotide primers were obtained that bind putative exons 1 to 8, 12, 18, and 23 (Protein Chemistry Laboratory, Table 1, FIG. 1). Genomic DNA from the RAW 264.7 murine macrophage cell line (H-$2^d$, ATCC TIB 71) (29) was used as a template.

Conditions for PCR: (93° C./5 min; 93° C./1 min, 68° C./10 min) for 16 cycles;

(93° C./1 min, 68° C./10 min plus 15 sec) for 12 cycles; 93° C./3 min.

The GeneAmp XL PCR kit (Perkin Elmer) which contains a mixture of thermostable DNA polymerases (rTth and Vent®) was used. Additional primers were as follows:

Lane 10:

sense—5' acac tacataCTTTATGCCACCAACAATGGCAAC 3' [SEQ ID NO: 13] and anti-sense—5' GGAGATAGGACAT-AGTTCAACATCTCC 3' [SEQ ID NO:15] primers in putative exons 7 and 12, respectively.

Lane 11:

sense primer of lane 10 and anti-sense primer—5' GGAT-GCTGCTGAGGGCTCTGTTGAGG 3' [SEQ ID NO: 16], in putative exons 7 and 18.

Lane 12:

sense primer of lane 10 and anti-sense primer—5' CTCAGGGAGCTGGAAGCCACTGACACTTCG 3' [SEQ ID NO: 17], in putative exons 7 and 23.

Amplicons were size fractionated on a 1% agarose gel.

Plasmid construction. A 7.0 kb amplicon spanning putative exons 4 to 7 was subcloned into the Bluescript SKII+ plasmid (Stratagene), using NotI and ClaI restriction sites that were added to the primers (30,31). PCR-derived insert was mapped using restriction endonucleases and partially sequenced using the di-deoxy sequencing method (32) and a Sequenase T7 DNA sequencing system (Amersham).

Exon 6 was opened using a partial SacI digest and the 1.7 kb phosphoglycerokinase (pgk)-neo cassette inserted (33–35). A 2.6 kb pgk-tk cassette was inserted 5' of exon 4 (33).

The long-arm spanned exons 4 to 6 (5.9 kb) and the short-arm spanned exons 6 to 7 (1.1 kb). This targeting vector was linearized at the NotI site.

Cells. Male E14 ES cells (36) were co-cultured on geneticin (G418) antibiotic-resistant murine embryonic fibroblasts (36–38) in high glucose DMEM nutrient culture medium (4.5 g/L; Gibco) supplemented with 15% fetal calf serum (Hyclone), glutamine (2 mM), non-essential amino acids (0.1 mM), penicillin (100 U/ml), streptomycin (100 μg/ml), 2-mercaptoethanol (50 μM), and leukemia inhibitory factor (1000 U/ml, Gibco) at 6% $CO_2$.

Transfection and selection. ES cells ($2 \times 10^7$ cells) were electroporated using the BTX 600 electroporation system (340 V, 100 μF, 0.4 cm gap) and 50 μg of NotI-linearized targeting vector. Electroporated cells were plated onto 10 cm dishes and selection initiated 24 hr later using 250 μg/ml G418 (Gibco) and 2 μM ganciclovir (Syntex). Colonies were picked on day 6.

Screening. Genomic DNA was isolated from ES clones and initially evaluated using PCR analysis. Primer 3, which is external to the short-arm but within exon 7 (5' GTTGC-CATTGTTGGTGGCATAAAG 3') [SEQ. ID NO: 12] and Primer 4, which is specific for the pgk-neo cassette (5' CGGTAGAATTATCGAATTCCTGCAGC 3') [SEQ.ID NO: 18] were used.

Accurate targeting events were determined by Southern blot analysis, using a 0.3 kd BamHI/NcoI genomic probe located external to the short-arm (probe A, FIG. 3), and a 1.7 kb pgk-neo probe (probe B, FIG. 3).

Genomic DNA was digested with EcoRI and/or HindIII, size-fractionated on a 0.7% agarose gel which was dried, pre-hybridized, hybridized using conventional techniques for in-gel Southern blot analysis (39–41). Gels were washed at 68° C. in 4×SSC/0.1% SDS followed by 0.1×SSC/0.1% SDS for 1 hr. Auto-radiograms were digitized using an HP ScanJet IIc/ADF scanner (Hewlett Packard), a PowerMac 7100/66, and Deskscan II software (Hewlett Packard).

RESULTS.

To determine where a pgk-neo selectable marker cassette could be placed in order to disrupt the NOS2 gene, the genomic organization of the murine locus was initially investigated.

A combination of Southern blot analysis and long-range PCR (23) was used to map genomic regions of interest.

Using the organization of the human NOS2 gene (24) the location of exons in murine cDNA sequence (26) was predicted (26).

The distance between putative exons was then mapped using genomic DNA template isolated from the RAW 264.7 murine macrophage cell line. Long-range PCR was performed using primer-pairs listed in Table 1 and FIG. 1.

Figure 1:
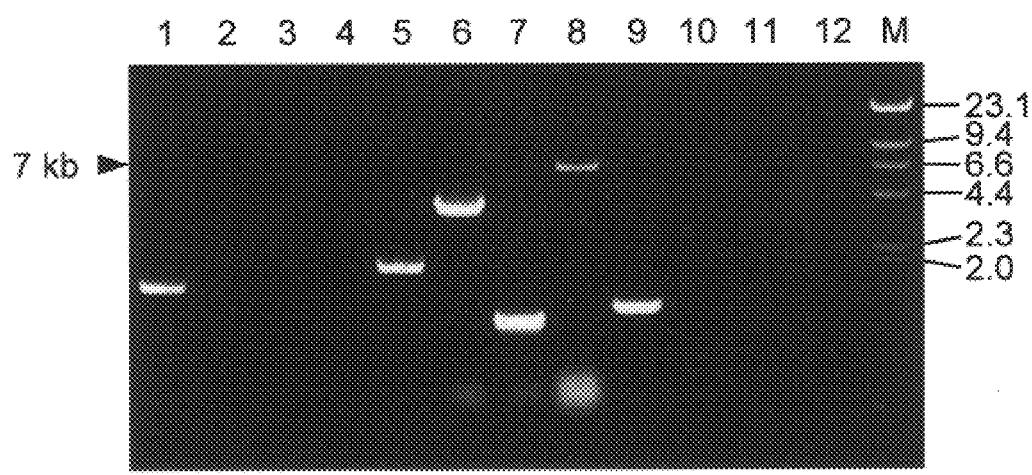
FIG. 1 shows: Mapping the murine NOS2 genomic locus using long-range PCR.

GeneAmp XL, a blend of thermostable DNA polymerases, was used to generate amplicons containing an intron flanked by a portion of exons containing primer-binding sites (FIG. 1).

The distance between exons 1 and 2 of the murine NOS2 gene is similar to that reported for the human locus (24). They are approximately 1.6 and 1.8 kb, respectively (lane 1, FIG. 1).

Distances between exons 2, 3, and 4 of the human NOS2 gene are approximately 1.1, 0.9, and 2.0 kb, respectively.

An amplicon using primers specific for putative exons 2 to 4 (lanes 2, 3, and 4; FIG. 1) could not be generated, although a 20 kb amplicon using control plasmid and primers provided with the GeneAmp XL kit was generated. The organization of exons 4 through 7 appears to be comparable between human and murine NOS2 genes.

The distances are approximately 1.2, 6.5, and 1.7 kb in the human NOS2 gene and are approximately 1.8, 4.1, and 1.1 kb in the murine gene (lanes 5, 6, and 7; FIG. 1).

To determine the capacity of this PCR system for generating genomic amplicons larger than 7 kb (lane 8, FIG. 1), primer-pairs from putative murine exons 7, 12, 18 and 23 were used because inter-exon distances are approximately 7.5, 15, and 22 kb in the human NOS2 gene (24).

That genomic amplicons were not obtained for this region of the murine NOS2 locus suggests the presence of differences in organization or the location of intron-exon boundaries compared to the human gene (lanes 10,11, and 12; FIG. 1).

PCR-based genomic mapping was further validated by comparing PCR-generated data about inter-exon distances to data obtained by Southern blot analysis (FIG. 2).

Murine genomic DNA was digested with EcoRI, HindIII or SacI and probed with a 0.3 kb DNA fragment used to screen ES cells (probe A, FIG. 3). This probe was derived from a 1.3 kb amplicon spanning putative exons 7 and 8 (lane 9, FIG. 1). Probe A detected approximately 8.5 kb EcoRI, 20 kb HindIII, and 4.0 kb SacI fragments on Southern blot analysis (panel A, FIG. 2).

The 8.5 kb distance predicted by PCR-mapping between the two EcoRI sites flanking putative exon 6 is the same length of the fragment detected by probe A on Southern blot analysis.

Further mapping of the region around probe A was done by performing double digests of murine genomic DNA using EcoRI and HindIII, EcoRI and SacI, or HindIII and SacI. The PCR-generated map predicts an approximately 5.6 kb EcoRI/HindIII, and a 2.2 kb EcoRI/SacI fragment. These fragment sizes are the same as those determined by Southern blot analysis.

For PCR-based gene targeting, a 7 kb amplicon flanked by portions of exons 4 and 7 (lane 8, FIG. 1) was generated. The pgk-neo positive selectable marker gene was inserted into putative exon 6 of this amplicon, at a SacI site (FIG. 3). This approach resulted in a 1.1 kb short-arm and a 5.9 kb long-arm of genomic DNA sequence homologous to the murine NOS2 chromosomal locus. The pgk-tk negative-selectable marker gene was placed 5' of exon 4.

Exon 6 of the NOS2 gene was targeted for the following reasons: The ability to generate a 7 kb amplicon between exons 4 and 7 using existing primer pairs initially prompted investigation of exons located within this region. There is presently no evidence for alternative splicing of murine NOS2 mRNA between exons 2 and 7 (6, 7, 42).

The binding domains for calmodulin (24), tetrahydrobiopterin (43), the flavin nucleotides FMN and FAD (24), and NADPH (44) are all 3' of exon 6.

Part of the heme binding site appears to be encoded by exon 6 (45). Thus, if disruption of the murine NOS2 gene at exon 6 results in a stable truncated protein, it should be non-functional.

PCR-based targeting vector linearized with NotI was then transfected into E14 ES cells using the electroporation method.

Following a 24 hr recovery period, cells were selected in media containing G418 and ganciclovir (GANC). Colonies resistant to G418 and GANC were picked, expanded, and screened from homologous recombinants by PCR analysis using a primer-pair specific for a region 3' of the short-arm of the targeting vector and for the pgk-neo cassette (Table 1, FIG. 3).

Clones found to be positive by PCR analysis were confirmed by Southern blot analysis using probes A and B (FIG. 3). In addition to the germline 8.5 kb EcoRI fragment, a new 2.4 kb EcoRI fragment was detected by probe A when targeting vector and chromosomal DNA undergo homologous recombination (Table 2, lane A in FIGS. 4A and 4B).

Double-digestion with EcoRI and HindIII resulted in a 5.6 kb germline fragment, whereas the 2.4 kb EcoRI new fragment was unchanged (Table 2, FIG. 4B). Digestion with HindIII generated an approximately 20 kb germline fragment which is difficult to resolve from the 19 kb fragment of the targeted allele (Table 2, FIG. 4C).

Probe B detects the transfected pgk-neo cassette and fragments of the endogenous pgk gene (Table 2). A 4.4 kb EcoRI and an approximately 4.3 kb HindIII fragment represent the endogenous pgk gene (Table 2, FIG. 5).

DNA from a correctly targeted clone, ROH.1, has the expected 8 kb EcoRI and approximately 19 kb HindIII fragments representing the targeted allele (Table 2, lane A of FIG. 5).

In contrast, the results of probing DNA from clone ROH.2 with probe B are consistent with a random insertion of the targeting construct. Approximately 4.3 kb EcoRI and 2.3 kb HindIII fragments are detectable by probe B (FIGS. 5A and 5B). No other bands were observed, suggesting that no additional copies of the targeting vector were integrated into the genome of these ES cell clones.

The targeting frequency of PCR-based gene targeting is of similar order-of-magnitude as conventional gene targeting (2,46).

In the first 41 double-resistant clones screened, four correctly targeted clones (Table 3) were identified.

Thus, approximately 1 of 10 double-resistant clones were accurately targeted using the PCR-based gene targeting method of the invention.

TABLE 1

PCR-based estimation of inter-exon distances in the murine NOS2 gene locus

| Gel Lane (FIG. 1) | Primer-pairs | | Putative Exons* | Amplicon Size (kb) |
|---|---|---|---|---|
| 1 | 5' gagaggcctAACTTCTCAGCCACCTTGG 3'-sense | [SEQ ID NO: 1] | 1–2 | 1.6 |
|   | 5' gagaggcctGCTGAGAACACACAAGG 3'-anti-sense | [SEQ ID NO: 2] | | |
| 2 | 5' ATGGCTTGCCCCTGGAAGT 3' | [SEQ ID NO: 3] | 2–3 | N.A. |
|   | 5' GAACATTCTGTGCTGTCCCAGTGAGGAGCTGC 3' | [SEQ ID NO: 4] | | |
| 3 | 5' gagtcgcgaCCGCAGCTCCTCACTGGGACAGCACAGAATGTTC 3' | [SEQ ID NO: 5] | 3–4 | N.A. |
|   | 5' GATGTGGCCTTGTGGTGAAG 3' | [SEQ ID NO: 6] | | |
| 4 | 5' ATGGCTTGCCCCTGGAAGT 3' | [SEQ ID NO: 3] | 2–4 | N.A. |
|   | 5' GATGTGGCCTTGTGGTGAAG 3' | [SEQ ID NO: 6] | | |
| 5 | 5' CTGGACAAGCTGCATGTGAC 3' | [SEQ ID NO: 7] | 4–5 | 1.8 |
|   | 5' CTGGTTGATGAACTCAATGGCATGAGGCAGGA 3' | [SEQ ID NO: 8] | | |
| 6 | 5' gagtcgcgaGCTCCTGCCTCATGCCATTGATTCATCAACCAG 3' | [SEQ ID NO: 9] | 5–6 | 4.1 |
|   | 5' tgtatcgatTTGGACCACTGGATCCTGCCGATGCAGCGAG 3' | [SEQ ID NO: 10] | | |
| 7 | 5' acactacgtaCTCGCTGCATCGGCAGGATCCAGTGGTC 3' | [SEQ ID NO: 11] | 6–7 | 1.1 |
|   | 5' GTTGCCATTGTTGGTGGCATAAAG 3' | [SEQ ID NO: 12] | | |

TABLE 1-continued

PCR-based estimation of inter-exon distances in the murine NOS2 gene locus

| Gel Lane (FIG. 1) | Primer-pairs | | Putative Exons* | Amplicon Size (kb) |
|---|---|---|---|---|
| 8 | 5' CTGGACAAGCTGCATGTGAC 3' | [SEQ ID NO: 7] | 4–7 | 7.0 |
|   | 5' GTTGCCATTGTTGGTGGCATAAAG 3' | [SEQ ID NO: 12] | | |
| 9 | 5' acac<u>tacgta</u>CTTTATGCCACCAACAATGGCAAC 3' | [SEQ ID NO: 13] | 7–8 | 1.3 |
|   | 5' ga<u>gatcgat</u>GTGAACTCCAAGGTGGCAGCATCC 3' | [SEQ ID NO: 14] | | |

*predictions based on human NOS2 genomic organization
N.A., no amplicon;
underlined, restriction sites;
lower-case, added sequence

TABLE 2

The length of predicted restriction fragments of the murine NOS2 locus in germline and targeted ES cells

| | Fragment Length (kb) | | | | |
|---|---|---|---|---|---|
| | probe A | | | probe B | |
| locus | EcoRI | EcoRI/HindIII | HindIII | EcoRI | HindIII |
| germline | 8.5 | 5.6 | 20 | 4.4* | 4.3* |
| targeted | 8.5 | 5.6 | 20 | 8.0 | 19 |
| | 2.2 | 2.2 | 19 | 4.4 | 4.3 |

*endogenous pgk gene

TABLE 3

Frequency of homologous recombination using PCR-based gene targeting

| | No. of cells or clones |
|---|---|
| electroporated | 2 × 10$^7$ |
| G418$^r$, GANC$^r$ | 826 |
| clones picked | 240 |
| clones screened | 41 |
| homologous recombinants | 4 |

$^r$resistant

Various other examples will be apparent to the person skilled in the art after reading the present disclosure without departing from the spirit and scope of the invention. It is intended that all such other examples be included within the scope of the claims appended hereto.

REFERENCES

1. Routtenberg, A. (1995) Nature 374, 314–315.
2. Soriano, P. (1995) Annu.Rev.Neurosci. 18, 1–18.
3. Bronson, S. K. & Smithies, O. (1994) J.Biol.Chem. 269, 27155–27158.
4. Melton, D. W. (1994) Bioessays 16, 633–638.
5. Shastry, B. S. (1994) Mol.Cell.Biochem. 136, 171–182.
6. Nathan, C. & Xie, Q. W. (1994) J.Biol.Chem. 269, 13725–13728.
7. Nathan, C. & Xie, Q. W. (1994) Cell 78, 915–918.
8. Robbins, J. (1993) Circ.Res. 73, 3–9.
9. Hasty, P. & Bradley, A. (1993) in Gene Targeting A Practical Approach, ed. Joyner, A. L. (IRL Press at Oxford University Press, Oxford), pp. 1–31.
10. Ramirez-Solis, R., Davis, A. & Bradley, A. (1993) in Guide to Techniques in Mouse Development, eds. Wasserman, P. M. & DePamphilis, M. L. (Academic Press, New York), pp. 855–878.
11. Thomas, K. R. & Capecchi, M. R. (1987) Cell 51, 503–512.
12. Kuida, K., Lippke, J. A., Ku, G., Harding, M. W., Livingston, D. J., Su, M. S. S. & Flavell, R. A. (1995) Science 267, 2000–2003.
13. Tarakhovsky, A., Muller, W. & Rajewsky, K. (1994) Eur.J.Immunol. 24, 1678–1684.
14. Lee, K. F., Li, E., Huber, L. J., Landis, S. C., Sharpe, A. H., Chao, M. V. & Jaenisch, R. (1992) Cell 69, 737–749.
15. Li, E., Bestor, T. H. & Jaenisch, R. (1992) Cell 69, 915–926.
16. Chisaka, O. & Capecchi, M. R. (1991) Nature 350, 473–479.
17. Kitamura, D., Roes, J., Kuhn, R. & Rajewsky, K. (1991) Nature 350, 423–426.
18. Mansour, S. L., Thomas, K. R., Deng, C. X. & Capecchi, M. R. (1990) Proc.Natl.Acad.Sci.USA 87, 7688–7692.
19. McMahon, A. P. & Bradley, A. (1990) Cell 62, 1073–1085.
20. Deng, C. & Capecchi, M. R. (1992) Mol.Cell.Biol. 12, 3365–3371.

REFERENCES (CONTINUED)

21. Hasty, P., Rivera-Perez, J. & Bradley, A. (1991) Mol.Cell.Biol. 11, 5586–5591.
22. te Riele, H., Maandag, E. R. & Berns, A. (1992) Proc.Natl.Acad.Sci.USA 89, 5128–5132.
23. Cheng, S., Fockler, C., Barnes, W. M. & Higuchi, R. (1994) Proc.Natl.Acad.Sci.USA 91, 5695–5699.
24. Chartrain, N. A., Geller, D. A., Kbty, P. P., Sitrin, N. F., Nussler, A. K., Hoffman, E. P., Billiar, T. R., Hutchinson, N. I. & Mudgett, J. S. (1994) J.Biol.Chem. 269, 6765–6772.
25. Geller, D. A., Lowenstein, C. J., Shapiro, R. A., Nussler, A. K., Di Silvio, M., Wang, S. C., Nakayama, D. K., Simmons, R. L., Snyder, S. H. & Billiar, T. R. (1993) Proc.Natl.Acad.Sci.USA 90, 3491–3495.
26. Xie, Q. W., Cho, H. J., Calaycay, J., Mumford, R. A., Swiderek, K. M., Lee, T. D., Ding, A., Troso, T. & Nathan, C. (1992) Science 256, 225–228.
27. Lowenstein, C. J., Glatt, C. S., Bredt, D. S. & Snyder, S. H. (1992) Proc.Natl.Acad.Sci.USA 89, 6711–6715.
28. Lyons, C. R., Orloff, G. J. & Cunningham, J. M. (1992) J.Biol.Chem. 267, 6370–6374.
29. Raschke, W. C., Baird, S., Ralph, P. & Nakoinz, I. (1978) Cell 15, 261–267.
30. Higuchi, R. (1989) in PCR Technology: Principles and Applications for DNA Amplifications, ed. Erlich, H. A. (Stockton, New York), pp. 61–70.
31. Scharf, S. J., Horn, G. T. & Erlich, H. A. (1986) Science 233, 1076–1078.
32. Sanger, F., Nicklen, S. & Coulson, A. R. (1977) Proc Natl Acad Sci USA 74, 5463–5467.

33. Tybulewicz, V. L., Crawford, C. E., Jackson, P. K., Bronson, R. T. & Mulligan, R. C. (1991) Cell 65, 1153–1163.
34. Soriano, P., Montgomery, C., Geske, R. & Bradley, A. (1991) Cell 64, 693–702.
35. Adra, C. N., Boer, P. H. & McBurney, M. W. (1987) Gene 60, 65–74.
36. Handyside, A. H., O'Neill, G. T. O., Jones, M. & Hooper, M. L. (1995) Roux's Arch. Dev. Biol. 198, 48–55.
37. Martin, G. R. & Evans, M. J. (1975) in Teratomas and Differentiation, eds. Sherman, M. I. & Solter, D. (Academic Press, New York), pp. 169–187.

REFERENCES (CONTINUED)

38. Doetschman, T. C., Eistetter, H., Katz, M., Schmidt, W. & Kemler, R. (1985) Journal of Embryology & Experimental Morphology 87, 27–45.
39. Lueders, K. K. & Fewell, J. W. (1994) Biotechniques 16, 66–67.
40. Tsao, S. G., Brunk, C. F. & Pearlman, R. E. (1983) Anal.Biochem. 131, 365–372.
41. Southern, E. M. (1975) J.Mol.Biol. 98, 503–517.
42. Dinerman, J. L., Lowenstein, C. J. & Snyder, S. H. (1993) Circ.Res. 73, 217–222.
43. Uvarov, V. Y. & Lyashenko, A. A. (1995) Biochem.Biophys.Res.Commun. 206, 736–741.
44. Xie, Q. W., Cho, H., Kashiwabara, Y., Baum, M., Weidner, J. R., Elliston, K., Mumford, R. & Nathan, C. (1994) J.Biol.Chem. 269, 28500–28505.
45. Chen, P. F., Tsai, A. L. & Wu, K. K. (1994) J.Biol.Chem. 269, 25062–25066.
46. Reaume, A. G., Desousa, P. A., Kulkarni, S., Langille, B. L., Zhu, D. G., Davies, T. C., Juneja, S. C., Kidder, G. M. & Rossant, J. (1995) Science 267, 1831–1834.
47. Ochman, H. Ajioka, J. W., Garza, D. & Hartl, D. L. (1989) in *PCR Technology: Principles and Applications for DNA Amplifications*, ed. Erlich, H. A. (Stockton, N.Y.) pp. 105–111.

What is claimed is:

1. A method of PCR-based gene targeting comprising:
   (a) obtaining a PCR-derived homologous genomic DNA fragment by applying long-range PCR to a murine genomic DNA template to generate a 7 kb genomic amplicon spanning exons 4 to 7 of the NOS2 gene locus consisting of a 1.1 kb short-arm spanning exons 6 to 7 and a 5.9 kb long-arm spanning exons 4 to 6 of said NOS2 gene locus by employing
      (i) a first oligonucleotide primer having a sequence specific for the 5' end of the target region and a suitable restriction site added at its 5' end and
      (ii) a second oligonucleotide primer having a sequence specific for the 3' end of the target region and a suitable restriction site added at its 3' end, whereby said primers bind to, respectively, the 5' and 3' ends of said target area,
   (b) producing a PCR-based targeting vector by
      (i) inserting the 1.7 kb pgk-neo positive selectable marker gene into said amplicon at a suitable restriction site within said target region and
      (ii) inserting the 2.6 kb pgk-neo negative selectable marker gene at the 5' or 3' end of said amplicon and then linearizing said targeting vector, and
   (c) thereafter transfecting said PCR-based targeting vector into ES cells whereby said targeting vector undergoes efficient homologous recombination into said gene locus.

2. A method of PCR-based gene targeting comprising:
   (a) obtaining a PCR-derived homologous genomic DNA fragment by applying long-range PCR to a murine genomic DNA template consisting of RAW 264.7 murine macrophage cell line to generate a large genomic amplicon spanning the exons of a gene locus of interest by employing
      (i) a first oligonucleotide primer having a sequence specific for the 5' end of the target region and a suitable restriction site added at its 5' end and
      (ii) a second oligonucleotide primer having a sequence specific for the 3' end of the target region and a suitable restriction site added at its 3' end, whereby said primers bind to, respectively, the 5' and 3' ends of said target area,
   (b) producing a aPCR-based targeting vector by
      (i) inserting the 1.7 kb pgk-neo positive selectable marker gene into said amplicon at a suitable restriction site within said target region and
      (ii) inserting the 2.6 kb pgk-tk negative selectable marker gene at the 5' or 3' end of said amplicon and then linearizing said targeting vector, and
   (c) thereafter transfecting said PCR-based targeting vector into ES cells whereby said targeting vector undergoes efficient homologous recombination into said gene locus.

3. A method of PCR-based gene targeting comprising:
   (a) obtaining a PCR-derived homologous genomic DNA fragment by applying long-range PCR to a murine genomic DNA template of RAW 264.7 murine macrophage cells to generate a large genomic amplicon spanning exons 4 to 7 of the NOS2 gene locus by employing
      (i) a first oligonucleotide primer having a sequence specific for the 5' end of said amplicon and a ClaI restriction site added at its 5' end and
      (ii) a second oligonucleotide primer having a sequence specific for the 3' end of said amplicon and a NotI restriction site added at its 3' end,
         whereby said primers bind to, respectively, the 5' and 3' ends of said amplicon,
   (b) producing a PCR-based targeting vector by
      (i) inserting the 1.7 kb pgk-neo positive selectable marker gene into said amplicon at a SacI restriction site at the 3' end of exon 6 of said amplicon and
      (ii) inserting the 2.6 kg pgk-tk negative selectable marker gene at a ClaI restriction site at the 5' end of exon 4 of said amplicon
      and then linearizing said targeting vector, and
   (c) thereafter transfecting said PCR-based targeting vector into ES cells whereby said targeting vector undergoes efficient homologous recombination into said NOS2 gene locus.

4. ES murine cells transfected with the PCR-based targeting vector produced by the method of claim 3.

* * * * *

```
                           SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:1:

GAGAGGCCTA ACTTCTCAGC CACCTTGG                                         28

(2) INFORMATION FOR SEQ ID NO:2:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:2:

GAGAGGCCTG CTGAGAACAC ACAAGG                                           26

(2) INFORMATION FOR SEQ ID NO:3:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:3:

ATGGCTTGCC CCTGGAAGT                                                   19
```

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:4:

GAACATTCTG TGCTGTCCCA GTGAGGAGCT GC                                    32

(2) INFORMATION FOR SEQ ID NO:5:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:5:

GAGTCGCGAC CGCAGCTCCT CACTGGGACA GCACAGAATG TTC                            43

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:6:

GATGTGGCCT TGTGGTGAAG                                                      20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:7:

CTGGACAAGC TGCATGTGAC                                                      20

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:8:

```
CTGGTTGATG AACTCAATGG CATGAGGCAG GA                                32
```

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:9:

```
GAGTCGCGAG CTCCTGCCTC ATGCCATTGA TTCATCAACC AG                     42
```

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:10:

```
TGTATCGATT TGGACCACTG GATCCTGCCG ATGCAGCGAG                        40
```

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:11:

```
ACACTACGTA CTCGCTGCAT CGGCAGGATC CAGTGGTC                          38
```

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:12:

```
GTTGCCATTG TTGGTGGCAT AAAG                                         24
```

(2) INFORMATION FOR SEQ ID NO:13:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:13:

ACACTACGTA CTTTATGCCA CCAACAATGG CAAC                    34

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:14:

GAGATCGATG TGAACTCCAA GGTGGCAGCA TCC                     33

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:15:

GGAGATAGGA CATAGTTCAA CATCTCC                            27

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:16:

GGATGCTGCT GAGGGCTCTG TTGAGG                             26

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:17:

CTCAGGGAGC TGGAAGCCAC TGACACTTCG                         30

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

-continued (xi) SEQUENCE DESCRIPTION: SEQ ID NO:18:

CGGTAGAATT ATCGAATTCC TGCAGC                                    26